United States Patent
Hegwood

(10) Patent No.: US 6,668,831 B1
(45) Date of Patent: Dec. 30, 2003

(54) APPLIANCE FOR A STOMA

(76) Inventor: Michael E. Hegwood, 6485 Saginaw, Memphis, TN (US) 38134

( * ) Notice: Subject to any disclaimer, the term of this patent is extended or adjusted under 35 U.S.C. 154(b) by 157 days.

(21) Appl. No.: 09/789,034

(22) Filed: Feb. 20, 2001

(51) Int. Cl.[7] ............................................. A61M 16/00
(52) U.S. Cl. ........................... 128/207.14; 128/200.26; 128/207.16; 128/205.27
(58) Field of Search ...................... 128/200.26, 207.14, 128/207.16, 207.29, 207.17, 912, 205.27, 202.27; 623/9; 606/108

(56) References Cited

U.S. PATENT DOCUMENTS

| | | | |
|---|---|---|---|
| 3,137,299 A | 6/1964 | Tabor | 128/351 |
| 3,827,440 A | 8/1974 | Birch et al. | 128/351 |
| 4,325,366 A | 4/1982 | Tabor | 128/207 |
| 4,971,054 A | 11/1990 | Andersson et al. | 128/207.16 |
| 5,048,518 A | 9/1991 | Eliachar et al. | 128/207.14 |
| 5,059,208 A | 10/1991 | Coe et al. | 623/9 |
| 5,062,420 A * | 11/1991 | Levine | 128/204.18 |
| 5,184,611 A * | 2/1993 | Turnbull | 128/200.26 |
| 5,201,309 A | 4/1993 | Friberg et al. | 128/207.14 |
| 5,259,376 A * | 11/1993 | Bales | 128/207.14 |
| 5,259,378 A | 11/1993 | Huchon et al. | 128/207.16 |
| 5,458,139 A * | 10/1995 | Pearl | 128/200.26 |
| 5,487,382 A | 1/1996 | Bezicot | 128/207.14 |
| 5,606,966 A * | 3/1997 | Smith | 128/200.26 |
| 5,738,095 A | 4/1998 | Persson | 128/207 |
| 5,806,515 A | 9/1998 | Bare et al. | 128/207.15 |
| 5,840,091 A * | 11/1998 | Strong | 128/207.14 |
| 5,848,590 A | 12/1998 | Smith | 128/201 |

FOREIGN PATENT DOCUMENTS

WO    WO 91/05579    * 5/1991    ............ 128/200.26

* cited by examiner

Primary Examiner—Weilun Lo
Assistant Examiner—Mital Patel
(74) Attorney, Agent, or Firm—Walker, McKenzie & Walker, P.C.

(57) ABSTRACT

A stoma appliance including a protective cover for attachment to a patient's neck adjacent a stoma; a housing member having a stoma tube for extending into the entrance of the stoma, and a body for positioning externally of the stoma; and a gasket for forming a seal between the protective cover and the housing member.

17 Claims, 9 Drawing Sheets

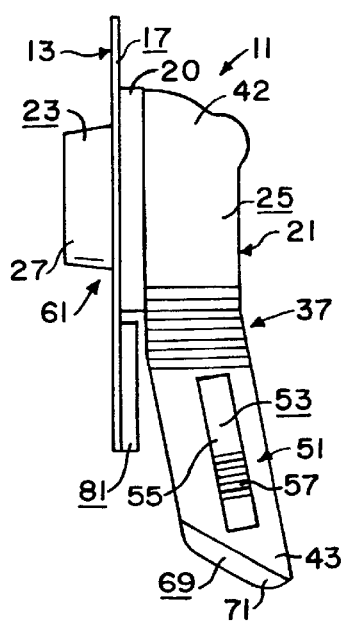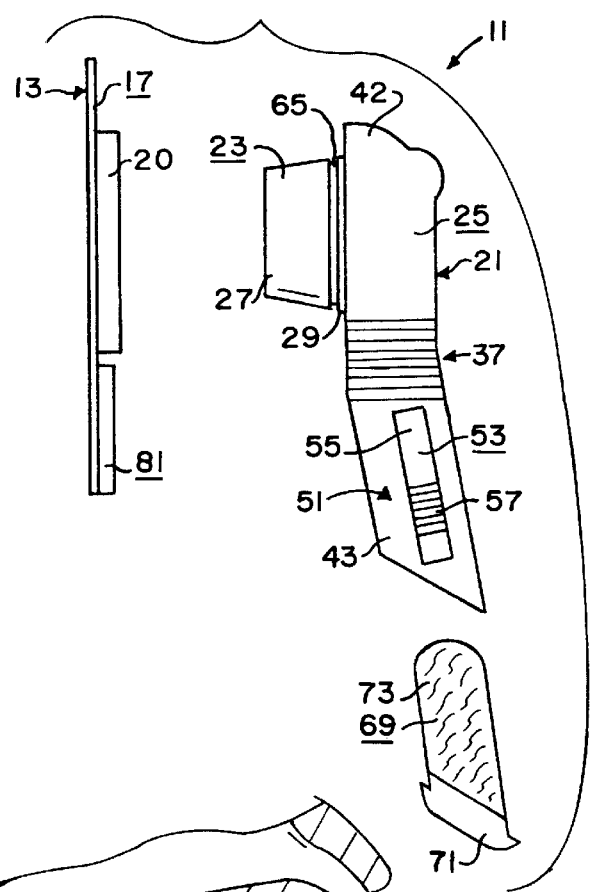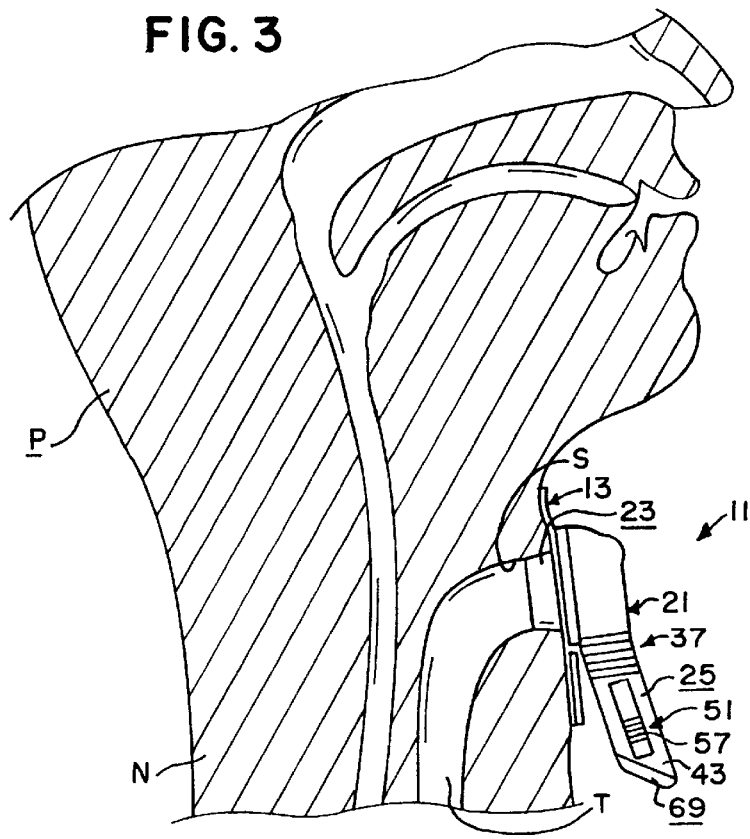

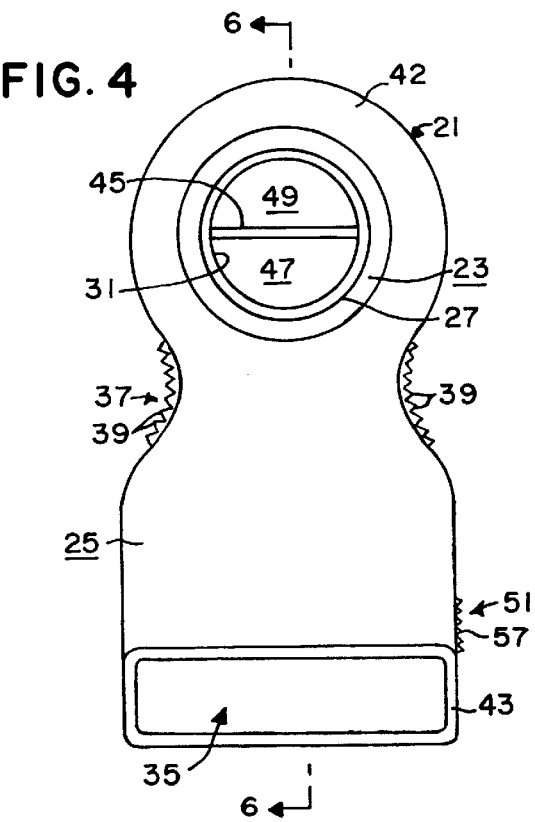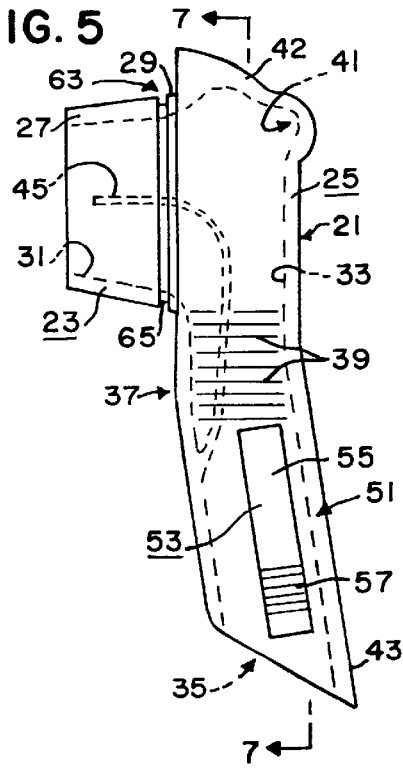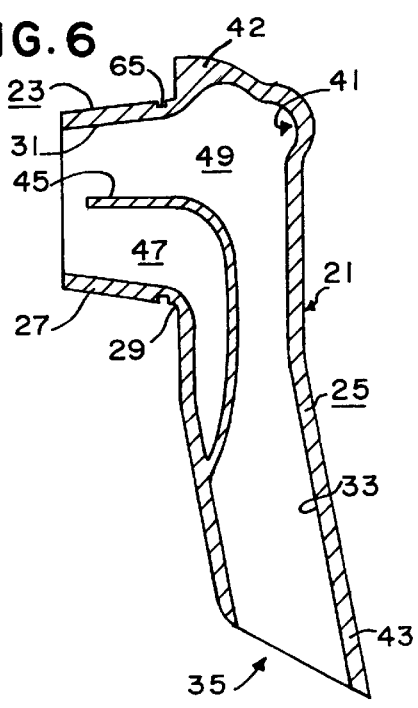

FIG. 8　　　　FIG. 9　　　　FIG. 10
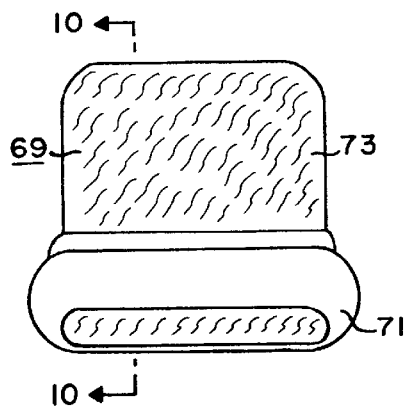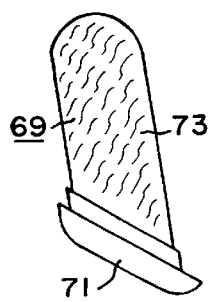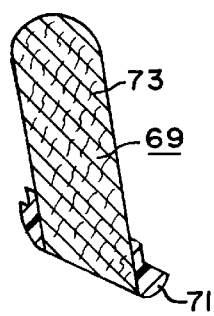
FIG. 11　　　FIG. 12　　　FIG. 13
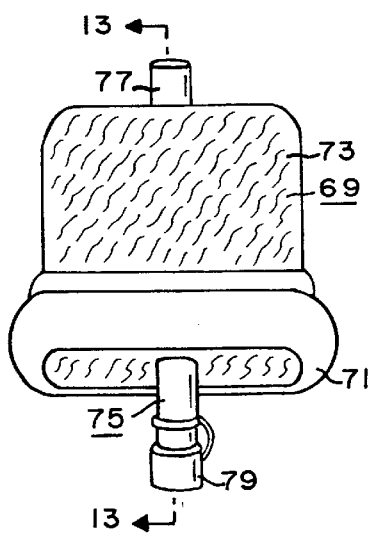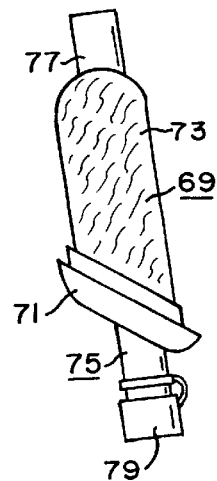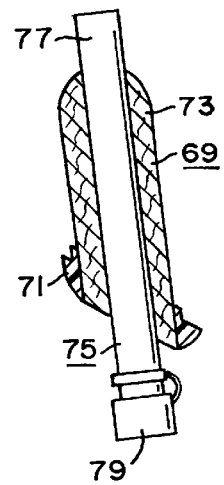
FIG. 14　　　　　　FIG. 15
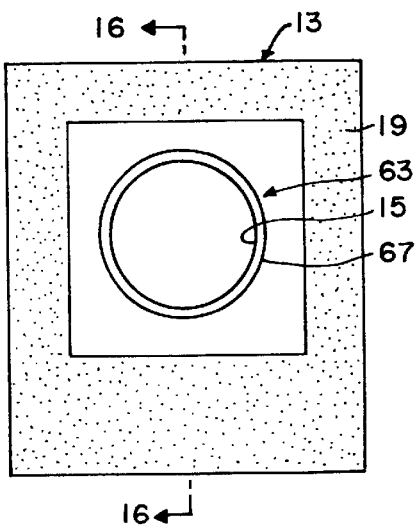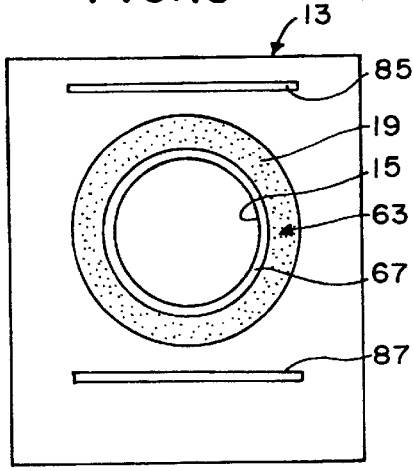

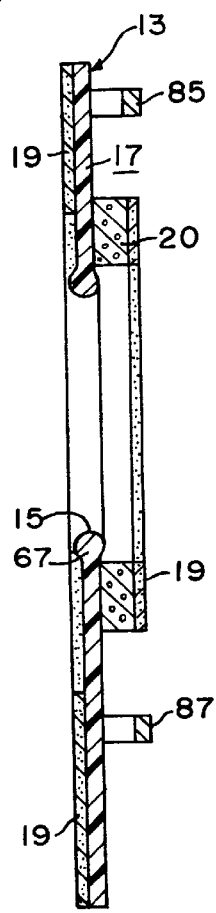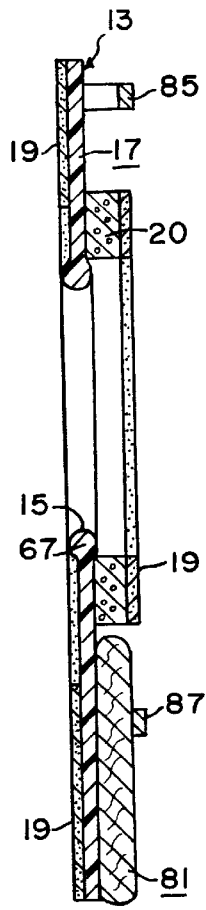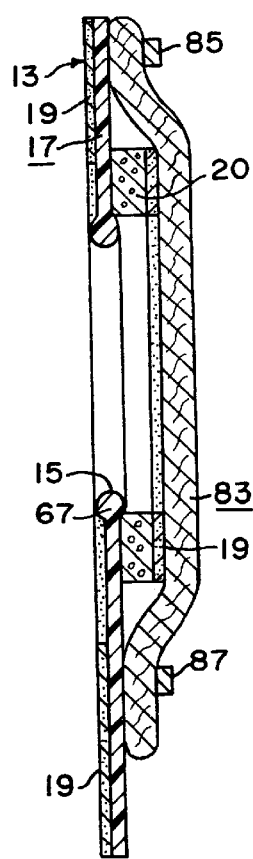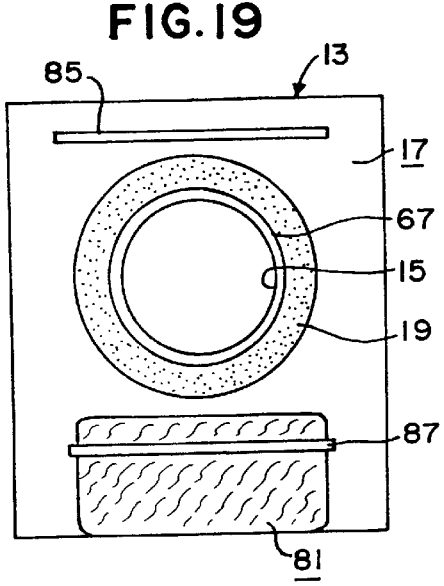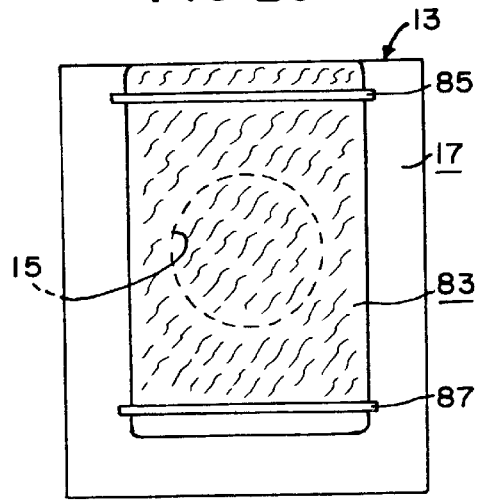

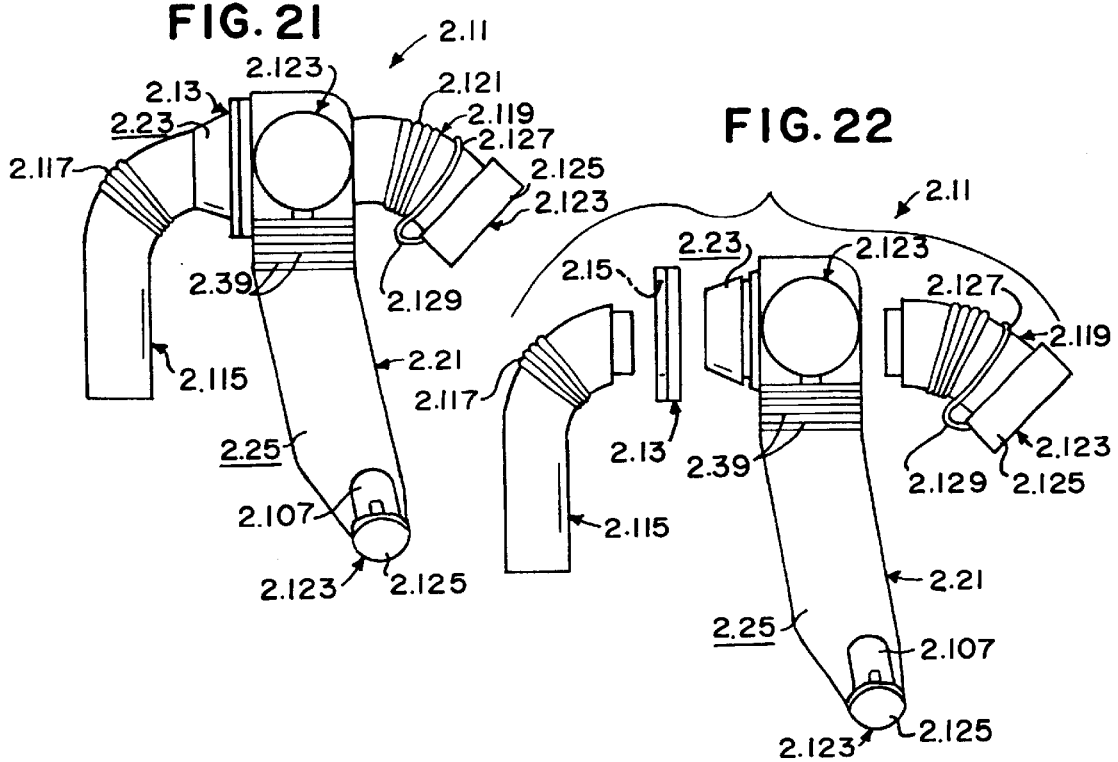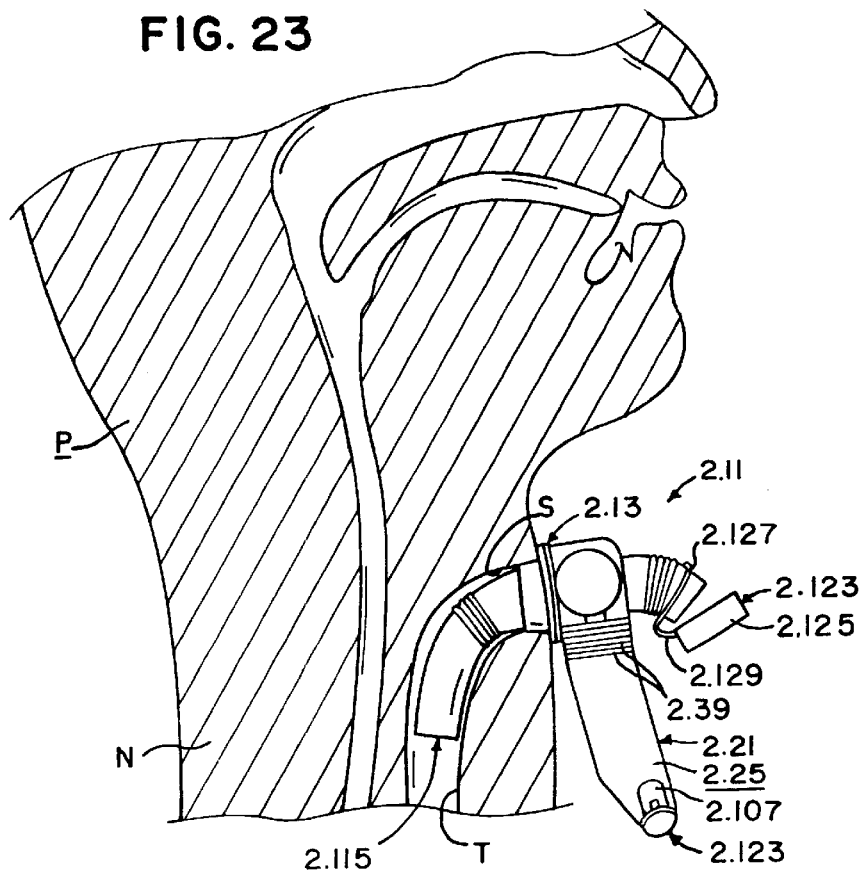

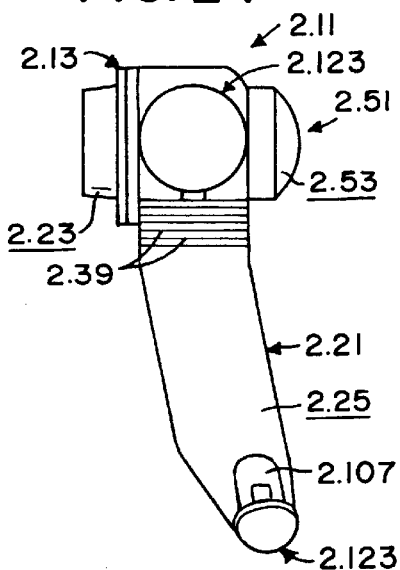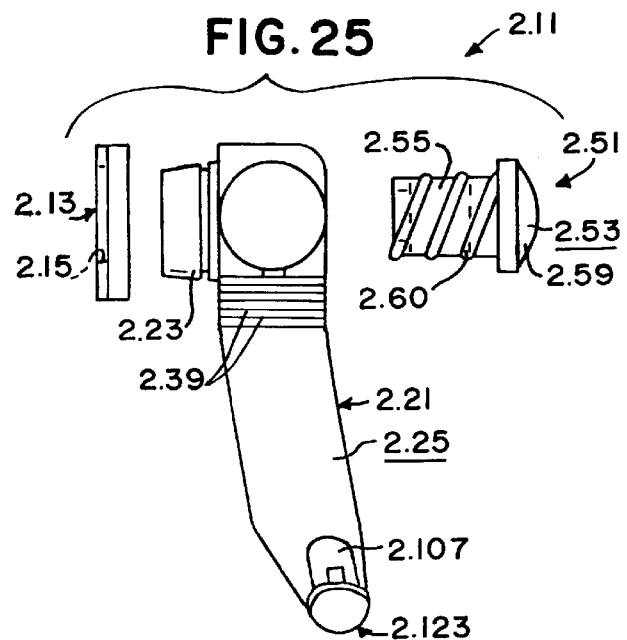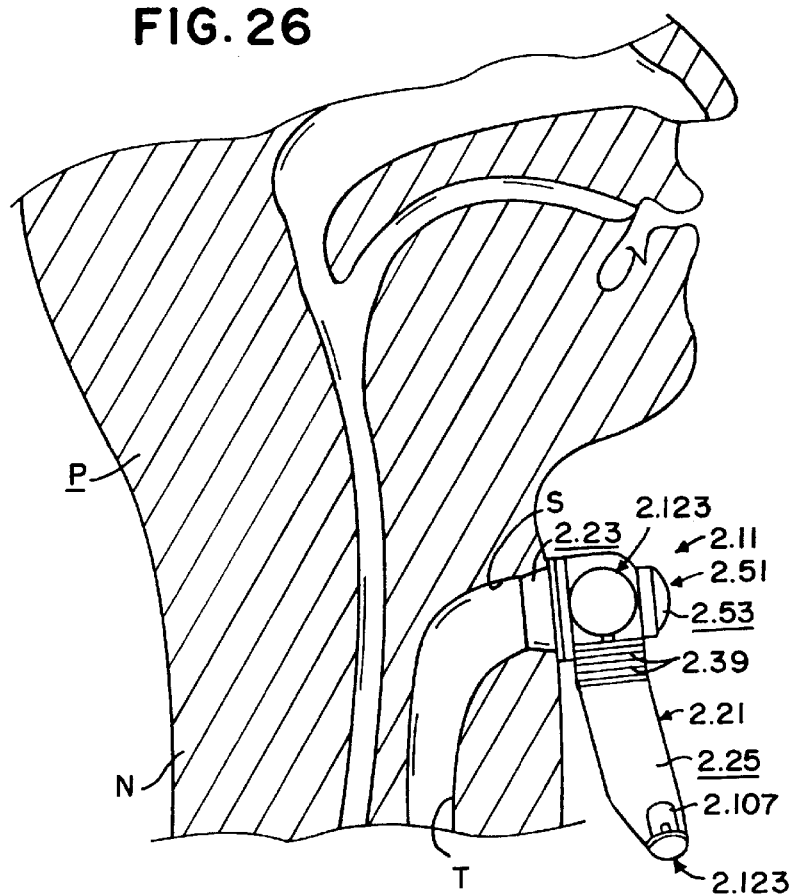

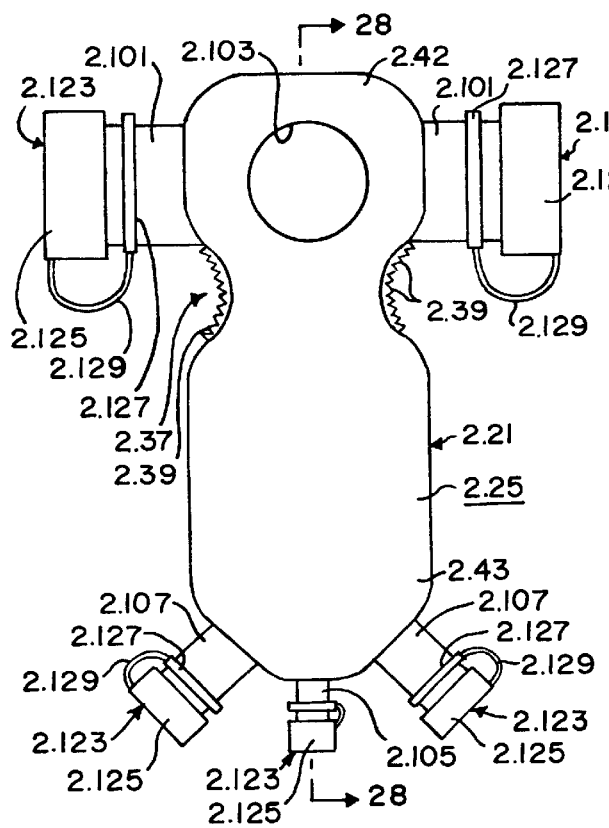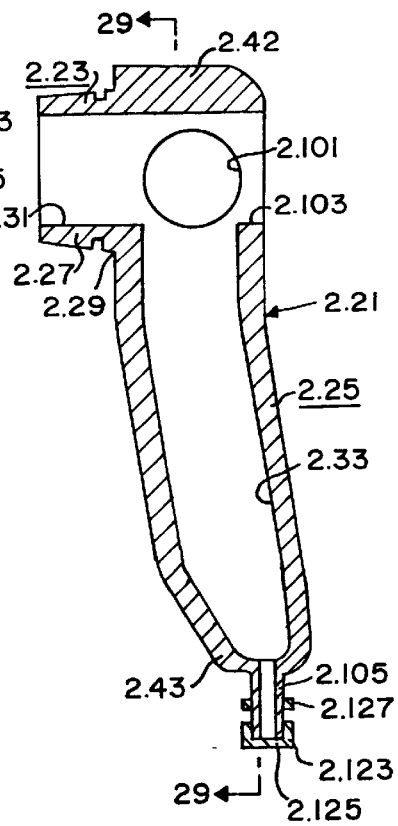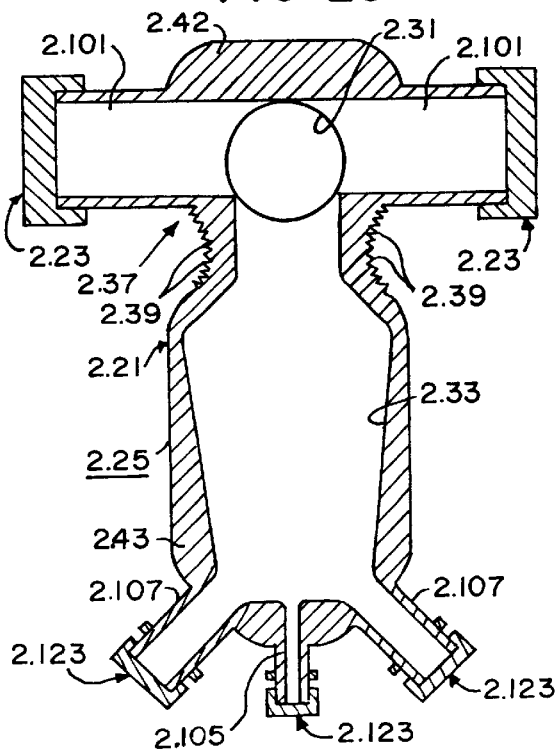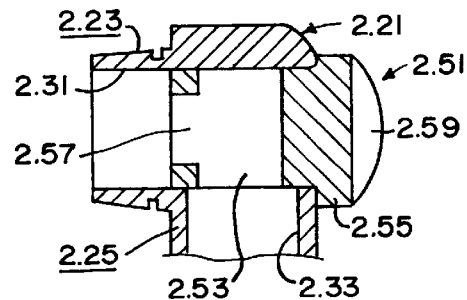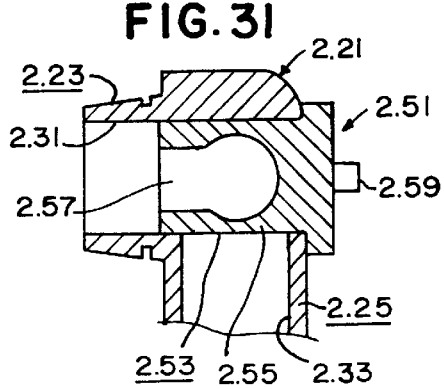

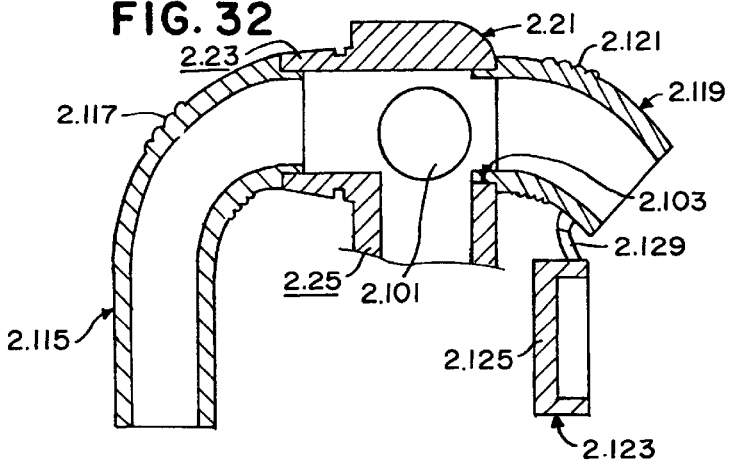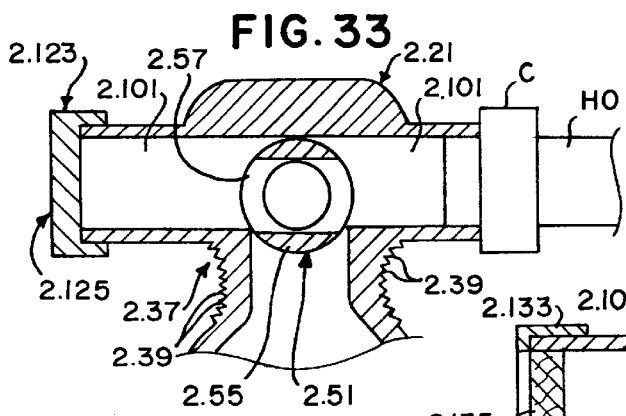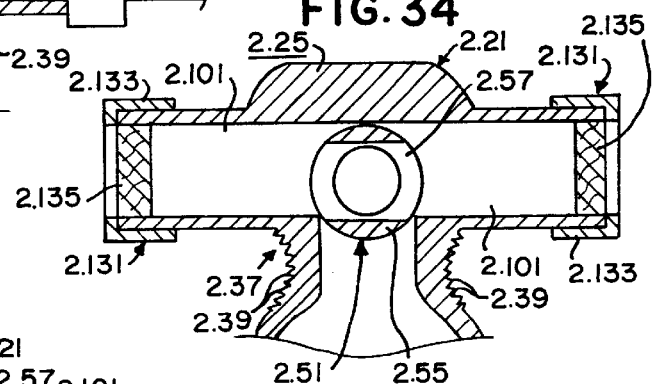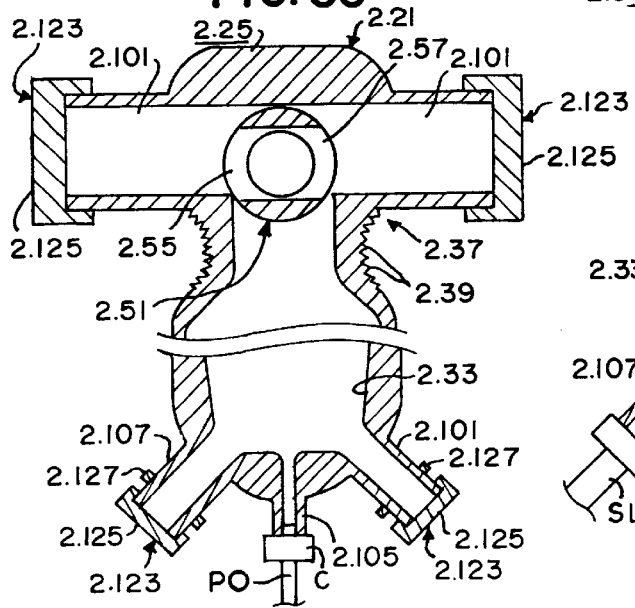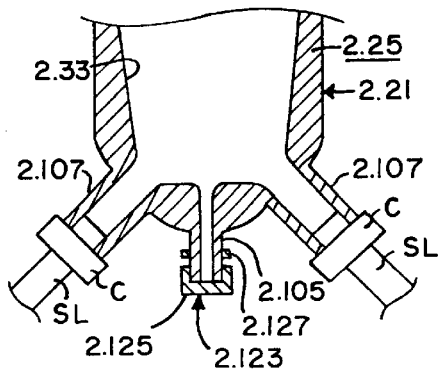

APPLIANCE FOR A STOMA

BACKGROUND OF THE INVENTION

1. Field of the Invention

The present invention relates, in general, to an appliance for use with a stoma, and, more specifically, to such an appliance that forms a seal about the stoma and that includes one or more accessories to control the passage of air therethrough.

2. Information Disclosure Statement

A laryngectomee patient will frequently wear a foam filter pad and a shower shield to protect the opening, or stoma, in the patient's throat through which the patient must breathe. Although the filter pad and shower shield functions adequately, it does present several problems. In rainy weather, the pad must be protected from getting wet. Coughing fluid from the patient's lungs necessitates frequent changing of the pad, and water typically enters around the sides and top of the shield when the patient turns his head while showering. Laryngectomee patients have long needed a device that adequately helps to prevent water from entering the stoma.

A preliminary patentability search conducted in class 128, subclasses 207.17, 207.16 and 207.14, produced the following patents which appear to be relevant to the present invention:

Tabor, U.S. Pat. No. 3,137,299, issued Jun. 16, 1964, discloses a tracheotomy tube having a valve designed to enable the patient to expel bronchial secretions by coughing.

Birch et al., U.S. Pat. No. 3,827,440, issued Aug. 6, 1974, discloses a removable check valve for installation on the external portion of a tracheotomy tube.

Tabor, U.S. Pat. No. 4,325,366, issued Apr. 20, 1982, discloses a tracheotomy tube with a valve designed to allow air to flow in either direction responsive to normal breathing through the tracheotomy tube while blocking air flow out the tracheotomy tube responsive to air flow above that present in normal breathing. A shower shield and filter can be used with the valve.

Andersson et al, U.S. Pat. No. 4,971,054, issued Nov. 20, 1990, discloses a breathing valve designed to filter an control the humidity of air inhaled via tracheotomies and tracheal tubes.

Eliachar et al., U.S. Pat. No. 5,048,518, issued Sep. 17, 1991, discloses a stoma stent system including a tubular stent for insertion into a trachea, and several plug components for insertion into an open end of the stent to progressively constrict air flow through the stent, transfer moisture from exhaled air to inhaled air, or redirect exhaled air toward the vocal cords, etc.

Coe et al., U.S. Pat. No. 5,059,208, issued Oct. 22, 1991, discloses a patient adjustable valve to control the flow of air through a stoma in the neck of the patient.

Friberg et al., U.S. Pat. No. 5,201,309, issued Apr. 13, 1993, discloses a housing for holding a replaceable laryngotomy tracheostomy filter, and a hood having a downwardly directed suction channel through which inhaled air has to pass before it reaches the filter.

Huchon et al., U.S. Pat. No. 5259,378, issued Nov. 9, 1993, discloses a tracheotomy device comprising a tracheotomy cannula, a non-return valve for permitting inhalation flow only, means connecting to a forced oxygenation device upstream of the valve, and two filter elements upstream of the valve.

Bezicot, U.S. Pat. No. 5,487,382, issued Jan. 30, 1996, discloses a tracheotomy filter device including a filter mass and a grill designed so that most mucus expelled from the trachea is prevented from reaching the filter mass.

Persson, U.S. Pat. No. 5,738 095, issued Apr. 14, 1998, discloses a tracheostoma device comprising a filter housing for receiving a moisture and heat exchanging filter and having a valve member spring biased to an opened position and adapted to be manually closed by means of a finger applied against the spring bias.

Bare et al., U.S. Pat. No. 5,806 515, issued Sep. 15, 1998, discloses an oxygen adapter for delivering low volume supplemental oxygen to tracheotomized patient using a conventional tracheostomy speaking valve.

Smith, U.S. Pat. No. 5,848,590, issued Dec. 15, 1998, discloses a tracheostoma filter comprising a housing and a filter component movable as a result of a pressure difference due to breathing between an inhalation position and an exhalation position, resulting in a change in resistance to breathing through the filter.

Nothing in the known prior art discloses or suggests the present invention. More specifically, nothing in the known prior art discloses or suggests a stoma appliance including (a) a protective cover for attachment to the patient's neck about the stoma, the protective cover having an aperture therethrough for positioning over the entrance of the stoma; (b) a housing member including a stoma tube for extending through the aperture in the protective cover and in the entrance of the stoma; and (c) a gasket for forming a seal between the protective cover and the housing member.

BRIEF SUMMARY OF THE INVENTION

The present invention provides a solution to numerous problems experienced by laryngectomee patients. A basic concept of the present invention is to provide a substantially waterproof appliance for covering a stoma and for allowing the passage of air through the stoma to be controlled.

The stoma appliance of the present invention includes, in general, (a) a protective cover for attachment to the patient's neck about the stoma, the protective cover having an aperture therethrough for positioning over the entrance of the stoma; (b) a housing member including a stoma tube for extending through the aperture in the protective cover and into the entrance of the stoma; and (c) a gasket for forming a seal between the protective cover and the housing member.

One object of the present invention is to provide a stoma appliance, including a protective cover and a housing member that can be removably sealed together.

Another object of the present invention is to provide a stoma appliance that is enclosed in a single unit with a filter that can be changed at anytime.

Another object of the present invention is to provide such a stoma appliance that has a chamber to hold mucus expelled from the patient's lungs.

Another object of the present invention is to provide such a stoma appliance that will filter the incoming air and, in so doing, will reduce heat and moisture and screen objects such as dust, dirt, bugs and other small particles.

Another object of the present invention is to provide such a stoma appliance that is sufficiently water proof so that the patient can shower with little or on problem.

Another object of the present invention is to provide a tracheostoma breathing aid for laryngectomee patients.

Another object of the present invention is to provide such a stoma appliance that has replaceable filters.

Another object of the present invention is to provide such a stoma appliance that has a drain tube, an oxygen tube and a clean-out tube at the bottom or lower end thereof.

Another object of the present invention is to provide such a stoma appliance that eliminates the necessity of having tubes inserted through the patient's nostrils.

Another object of the present invention is to provide such a stoma appliance that sticks on and may be removed easily.

Another object of the present invention is to provide such a stoma appliance that allows easy oxygen supplementation.

Another object of the present invention is to provide such a stoma appliance that allows great airflow into the patient's lungs.

Another object of the present invention is to provide such a stoma appliance that helps hospitalized laryngectomee patients avoid numerous hookups.

BRIEF DESCRIPTION OF THE SEVERAL VIEWS OF THE DRAWINGS

FIG. 1 is a side elevational view of the stoma appliance of the present invention, showing one embodiment of the housing member thereof.

FIG. 2 is an exploded view of the appliance of FIG. 1.

FIG. 3 is a diagrammatic view of the appliance of FIG. 1, shown associated with a patient's stoma.

FIG. 4 is a rear elevational view of the housing member of the appliance of FIG. 1.

FIG. 5 is a side elevational view of the housing member of FIG. 4.

FIG. 6 is a sectional view substantially as taken on line 6—6 of FIG. 4.

FIG. 7 is a sectional view substantially as taken on line 7—7 of FIG. 5.

FIG. 8 is a rear elevational view of the filter of the appliance of FIG. 1.

FIG. 9 is a side, elevational view of the filter of FIG. 8

FIG. 10 is a sectional view substantially as taken on line 10—10 of FIG. 8.

FIG. 11 is a rear elevational view of a modified embodiment of the filter of FIG. 8.

FIG. 12 is a side elevational view of the filter of FIG. 11.

FIG. 13 is a sectional view substantially as taken on line 13—13 of FIG. 11.

FIG. 14 is a rear elevational view of the protective cover of the appliance of FIG. 1.

FIG. 15 is a front elevational view of the protective cover of FIG. 14.

FIG. 16 is a sectional view substantially as taken on line 16—16 of FIG. 14.

FIG. 17 is a sectional view similar to FIG. 16 but showing a first pad attached thereto.

FIG. 18 is a sectional view similar to FIG. 16 but showing a second pad attached thereto.

FIG. 19 is a front elevational view of the construct of FIG. 17.

FIG. 20 is a front elevational view of the construct of FIG. 18.

FIG. 21 is a side elevational view of the stoma appliance of the present invention, showing another embodiment of the housing member thereof and showing an airway tube with a flexible elbow and an airway access tube coupled therewith.

FIG. 22 is an exploded view of the appliance FIG. 21.

FIG. 23 is a diagrammatic view of the appliance of FIG. 21 shown associated with a patient's stoma.

FIG. 24 is a side elevational view of the stoma appliance of the present invention, with the housing member of FIG. 21 and showing an a valve with a rotatable gate combined therewith.

FIG. 25 is an exploded view of the appliance FIG. 23

FIG. 26 is a diagrammatic view of the appliance of FIG. 24 shown associated with a patient's stoma.

FIG. 27 is a rear elevational view of the housing member of the appliances of FIGS. 21 and 24.

FIG. 28 is a sectional view substantially as taken on line 28—28 of FIG. 27.

FIG. 29 is a sectional view substantially taken on line 29—29 of FIG. 28.

FIG. 30 is a sectional view similar to a portion of FIG. 28 but including a valve having a rotatable gate combined with the housing member and with the rotatable gate shown in a first position.

FIG. 31 is a sectional view similar to FIG. 30 but showing the rotatable gate in a second position.

FIG. 32 is a sectional view similar to a portion of FIG. 28 but including an airway tube and an airway access tube combined with the housing member.

FIG. 33 is a sectional view similar to a portion of FIG. 29 but including the valve of FIG. 30 with the rotatable gate shown in the second position and showing a gas supply line coupled thereto.

FIG. 34 is a sectional view similar to FIG. 33 but showing two filter members coupled thereto rather than a gas supply line.

FIG. 35 is a sectional view similar to portions of FIG. 29 including the valve of FIG. 30 with the rotatable gate shown in the first position and showing a portable gas supply line coupled thereto.

FIG. 36 is a sectional view similar to a portion of FIG. 35 but showing two drainage lines coupled thereto rather than a portable gas supply line.

DETAILED DESCRIPTION OF THE INVENTION

Figure 37:
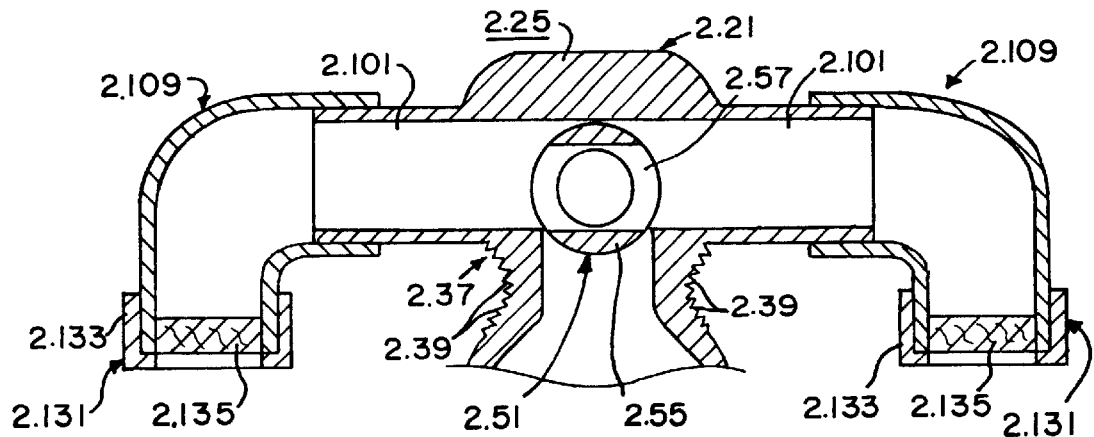
FIG. 37 is a sectional view similar to FIG. 33 but showing two 90° elbows both terminating in filter members coupled thereto rather than a gas supply line.
Figure 38:
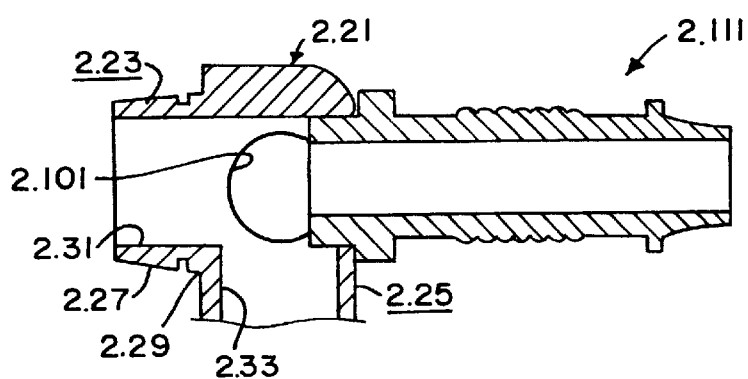
FIG. 38 is a sectional view similar to a portion of FIG. 28 but including a flexible airway mouthpiece combined with the housing member.

The present invention consists of an appliance for use by a patient P having a stoma S extending through the patient's neck N into the patient's trachea T. The appliance may be used by a patient P having a tracheostomy (any construction of an artificial opening, or stoma, through the neck N into the trachea T for the relief of difficulty in breathing, etc.), and is especially d for a patient P having a full laryngectomy (the surgical removal of the larynx with the upper portion of the trachea T being brought out the front of the neck N to create the stoma S and permanently close the natural passageway between the upper portion of the trachea T and the patient's throat), etc.

A first preferred embodiment of the appliance of the present invention is shown, in general, in FIGS. 1–3, and identified by the numeral 11.

The appliance 11 includes a protective cover 13 for attachment to the patient's neck N adjacent the stoma S. The protective cover 13 has an aperture 15 therethrough for positioning over the entrance or mouth of the stoma S when the protective cover 13 is attached to the patient's neck N adjacent the stoma S so that the protective cover 13 extends around or fully surrounds the mouth of the stoma S. The protective cover 13 preferably includes a sheet 17 of waterproof or substantially waterproof material (i.e., any plastic or the like typically used for medical dressings and the like such as the well known "Tegaderm" brand medical dressing made by 3M Health Care, St. Paul, Minn. 55144-1000, or the like) having an adhesive coating 19 at least partially covering one side for secure attachment to the patient's skin. The protective cover 13 may include a cushion 20 surrounding the aperture 15. A portion adhesive coating 19 may be provided on the outer side of the cushion 20. The protective cover 13 may have various additional features and embodiments as will now be apparent to those skilled in the art.

The appliance 11 includes a housing member 21. The housing member 21 includes a stoma tube 23 for positioning internally of the stoma S, and a body 25 for positioning externally of the stoma S.

The stoma tube 23 has a first end 27 for extending into the entrance or mouth of the stoma S, a second end 29 located remote from the first end 27, and a cavity 31 extending between the first and second ends 27, 29 thereof. The exterior of the stoma tube 23 is preferably tapered from a larger measurement at the second end 29 thereof to a smaller measurement at the first end 27 thereof to allow the stoma tube 23 to be easily inserted into the stoma S and to allow an easy "Morser taper" type insertion, attachment and seal between the exterior of the stoma tube 23 and the wall of the stoma S.

The body 25 of the housing member 21 is attached to the second end 29 of the stoma tube 23 and has a cavity 33 communicating with the cavity 31 of the stoma tube 23 and has an airway opening 35 communicating with the cavity 33 to allow air to enter the cavity 33 and pass from the cavity 33, through the cavity 31 and into the trachea T. As shown in FIGS. 4 and 7, the body 25 of the housing member 21 preferably has an generally oblong, "hourglass" shape when viewed from the front or rear elevation, with a relatively narrow waist or recess 37 to allow the body 25 to be easily gripped between, for example, the thumb and forefinger of the patient P for insertion or removal of the housing member 21, etc. Grooves or ribs 39 are preferably formed in the sides of the waist 37 of the body 25 to allow the unit to be held firmly.

The cavity 33 of the body 25 preferably has a protuberant portion or bubble 41 formed adjacent the upper end 42 thereof with the stoma tube 23 positioned generally at a right angle to the bubble 41 and with the airway opening 35 formed a the lower end 43 of the body 25. The upper and lower ends 42, 43 of the body 25 are defined with the appliance 11 attached to the patient's stoma S and with the patient P in an upright standing or seated position as shown in FIG. 3. The function of the bubble 41 is to form an air deflection means or structure within the cavity 33 to deflect air back to the portion of a typical voice prosthesis or the like that may be located within the stoma S and may be adjacent the first end 27 of the stoma tube 23.

The housing member 21 preferably includes a divider wall 45 within the cavity 33 of the body 25 for dividing the cavity 33 into a discharge chamber 47 for receiving waste (e.g., mucus) through the stoma tube 23 from the patient's trachea T, and an airway chamber 49 for allowing air to pass from the airway opening 35 of the body 25 through the cavities 33, 31 of the body 25 of the housing member 25 and the stoma tube 23 of the housing member 21 and into the patient's trachea T. The divider wall 45 should extend to the cavity 31 of the stoma tube 23 and preferably extends at least partway into the cavity 31 of the stoma tube 23 as clearly shown in FIG. 6.

The appliance 11 preferably includes a valve 51 for controlling the passage of air between the airway opening 35 of the body 25, the cavity 33, and the cavity 31 of the stoma tube 23. The valve 51 preferably includes a slidable gate 53 for movement between a fully opened position as shown in solid lines in FIG. 7 in which the passage of air through the cavity 33 is unimpeded, and a fully closed position as shown in broken lines in FIG. 7 in which the passage of air through the cavity 33 is blocked. The slidable gate 53 preferably includes a tongue portion 55 for selectively extending across the cavity 33 to block the passage of air therethrough and a tab or grip portion 57 attached to the tongue portion 55 for being easily engaged by the patient's thumb or finger to allow the patient P to easily slide the tongue portion 55 back and forth between opened and closed positions. The grip portions 57 may include grooves or the like on the face thereof to allow the patient P to firmly grip it. The body 25 preferably includes guide means 59 for guiding the tongue portion 55 between the opened and closed positions. The guide means 59 may consist of channels or furrows either cut into opposite walls of the body 25 within the cavity 33 thereof, or formed between a pair of spaced ridges or ribs extending from the opposite walls of the body 25 within the cavity 33 thereof (see FIGS. 6 and 7).

The housing member 21 may be constructed in various manners and out of various materials as will now be apparent to those skilled in the art. Thus, for example, the stoma tube 23 and body 25 of the housing member 21 can be molded or otherwise constructed as a one-piece, integral unit out of a medical grade, physiologically acceptable plastic or the like, in various colors, and in various sizes to fit a range of typical patients, or may be custom designed for a specific patient, etc. The slidable gate 53 of the valve means 51 may also be molded or otherwise constructed as a one-piece, integral unit out of the same medical grade, physiologically acceptable plastic or the like, in various sizes to fit specific housing members 21, etc.

The appliance 11 includes a seal or gasket 61 for forming a seal between the protective cover 13 and the housing member 21. The gasket 61 preferably includes an O-ring means 63 for tightly securing the protective cover 13 to the housing member 21. The O-ring means 63 preferably includes groove means 65 in the second end 29 of the stoma tube 23 of the housing member 21, and includes an O-ring 67 for coacting with the groove means 65 to clamp the edge of the aperture 15 of the protective cover 13 to the stoma tube 23 of the housing member 21. The O-ring 67 and the protective cover 13 may be made as an integral, one-piece construct. On the other hand, the O-ring 67 could be separate from the protective cover 13 and used to surround a portion of the protective cover 13 adjacent the aperture 15to clamp that portion of the protective cover 13 to the stoma tube 23. Optionally, a groove could be formed in the mouth of the aperture 15 and a male ring could be formed on the second end 29 of the stoma tube 23 to coact with the groove in the mouth of the aperture 15 to form a seal between the protective cover 13 and the housing member 21 and tightly secure the protective cover 13 and the housing member 21 together.

The appliance 11 preferably includes filter means 69 for filtering air passing thorough the airway opening 35 of the body 25 of the housing member 21 to remove any suspended impurities or solids in the air entering the airway opening 35. The filter means 69 may include a base portion 7 for being attached to the airway opening 35 of the body 25, and a filter media portion 73 attached to the base portion 71. The base portion 71 may be molded or otherwise constructed out of plastic in a design for being snapped onto the body 25 over the airway opening 35. For example, the mouth of the airway opening 35 of the body 25 may have a groove extending therearound and the edge of the base portion 71 of the filter means 69 may have a raised notch or ridge extending therearound for snapping into the groove in the mouth of the airway opening 35 to removably secure the filter means 69 to the body 25 so that the entire filter means 69 can be removed from the body 25 and either the entire filter means 69 or just the filter media portion 73 can be replaced when needed or desired. The base portion 71 preferably includes an element face consisting of an pen grid for holding the filter media portion 73 in place while allowing airflow therethrough.

An oxygen connection 75 may coupled with the filter means 69 for allowing pressurized oxygen from a typical portable pressurized oxygen supply means to flow into the cavity 33 of the body 25 of the ho sing member 21. The oxygen connection 75 preferably includes a tube 77 extending through the filter means 69, and a solid cap 79 for selectively closing the tube 77. The oxygen connection 75 allows the patient P to be attached to a portable oxygen system and moved at anytime. The oxygen connection 75 can be extended. One use for the oxygen connection 75 is in emergency situations such as in an airplane emergency when all passengers need to use supplemental oxygen and oxygen face masks are supplied. Since such face masks are not effective for laryngectomee patients who breath through the stoma S, the oxygen connection 75 allows the oxygen supply tube supplying air to a face mask to be pulled from the face mask and connected to the tube 77, thereby supplying oxygen to the patient P.

The appliance 11 may include a discharge debris pad 81 for attachment to the protective cover 13 below the aperture 15 therethrough for trapping discharge debris from the stoma S, and a stoma cover pad 83 for covering the stoma S. The discharge debris pad 81 is preferably sized to cover just a portion of the protective cover 13 below the aperture 15 while the stoma cover pad 83 is preferably sized to cover thee entire aperture 15 as well as a portion of protective cover 13 both below and above the aperture 15. The discharge debris pad 81 is designed to be used in combination with the housing member 21 while the stoma cover pad 83 is designed to cover the mouth of the stoma S when the housing member 21 is not being used (e.g., during nighttime sleep, etc.). The discharge debris pad 81 is preferably made of a mesh or gauze while the stoma cover pad 83 could be made of various materials such as, for example, any mesh or gauze typically used for surgical dressings. The protective cover 13 may include a loop member for holding the discharge debris pad 81. Preferably, the protective cover 13 includes an upper loop member 85 and a lower loop member 87 whereby the lower loop member 87 can be used to hold the discharge debris pad 81 just below the aperture 15, and whereby both the upper and lower loop members 85, 87 can be used to removably hold the stoma cover pad 83 over the aperture 15.

To use the appliance 11 the protective cover 13 is attached to the patient's neck N with the aperture 15 through the protective cover 13 positioned over the mouth of the stoma S. The first end 27 of the stoma tube 23 can then be inserted into the stoma S until the gasket forms a seal between the protective cover 13 and the housing member 21. With the filter means 69 attached to the body 25 of the housing 21, the patient P can adjust the flow of air into his/her lungs by merely sliding the tab portion 57 of the slidable gate 53 of the valve 51 back and forth. The housing member 21 can be easily removed to clean the discharge chamber 47, etc., merely be gripping the body 25 about the waist 37 and pulling the stoma tube 23 out of the stoma S. The filter means 69 can be removed and replaced, etc., while the housing 21 is in-place. If it might be necessary to give the patient P oxygen, the filter means 69 with the oxygen connection 75 is attached to the body 25 to allow a line from a portable oxygen tank or the like to be easily connected to the tube 77 if desired.

A second preferred embodiment of the appliance of the present invention is shown, in general, in FIGS. 21–26, and identified by the numeral 2.11.

The appliance 2.11 includes a protective cover 2.13 for attachment to the patient's neck N adjacent the stoma S. The protective cover 2.13 is substantially similar to the protective cover 13 of the appliance 11 and has an aperture 2.15 therethrough for positioning over the entrance or mouth of the stoma S when the protective cover 2.13 is attached to the patient's neck N adjacent the stoma S so that the protective cover 2.13 extends around or fully surrounds the mouth of the stoma S. The basic difference between the protective cover 2.13 and the protective cover 13 is the dimensions thereof, with the protective cover 2.13 being more strip like as clearly shown in the drawings. However, the basic function and construction of the protective cover 2.13 is the same as the protective cover 13 and reference should be made to the above disclosure of the protective cover 13 for a complete and thorough understanding of the construction and function of the protective cover 2.13.

The appliance 2.11 includes a housing member 2.21. The housing member 2.21 includes a stoma tube 2.23 for positioning internally of the stoma S, and a body 2.25 for positioning externally of the stoma S.

The stoma tube 2.23 has a first end 2.27 for extending into the entrance or mouth of the stoma S, a second end 2.29 located remote from the first end 2.27, and a cavity 2.31 extending between the first and second ends 2.27, 2.29 thereof. The basic function and construction of the stoma tube 2.23 is the same as the stoma tube 23 and reference should be made to the above disclosure of the stoma tube 23 for a complete and thorough understanding of the construction and function of the stoma tube 23.

The body 2.25 of the housing member 2.21 is attached to the second end of the stoma tube 2.23 and has a cavity 2.33 communicating with the cavity of the stoma tube 2.23. As shown in FIGS. 21–29, the shape of the body 2.25 of the housing member 2.21 is basically similar to the shape of the body 25 of the housing member 21. Thus, the body 2.25 preferably has an generally oblong, "hourglass" shape when viewed from the front or rear elevation, with a relatively narrow waist or recess 2.37 to allow the body 2.25 to be easily gripped between, for example, the thumb and forefinger of the patient P for insertion or removal of the housing member 2.21, etc. Grooves or ribs 2.39 are preferably formed in the sides of the waist 2.37 of the body 2.25 to allow the unit to be held firmly.

A basic difference between the body 25 of the housing member 21 and the body 2.25 of the housing member 2.21 is the location and design of the airway opening communicating with the cavity 2.33 to allow air to enter the cavity 2.33 and pass from the cavity 2.33, through the cavity of the stoma tube 2.21 and into the trachea T. Thus, rather than having a single airway opening 35 at the lower end 43 of the body 25, the body 2.25 has a side port 2.101 extending outward of each side of the body 2.25 adjacent the upper end 2.42 thereof to form a generally T-shaped configuration at the upper end 2.42 of the body 2.25, and a center port 2.103 in the center front of the upper end 2.42 thereof substantially between the airway openings 2.35 and aligned with the cavity 2.31 of the stoma tube 2.23 to combine with the side ports 2.101 to provide a plurality of multi-use ports for reasons which will hereinafter become apparent. As with the body 25, the upper and lower ends 2.42, 2.43 of the body 2.25 are defined with the appliance 2.11 attached to the patient's stoma S and with the patient P in an upright straining or seated position. Also the body 2.25 preferably has a plurality of ports at the lower end 2.43 thereof. For example, the body 2.25 may have a bottom center, or oxygen connection, port 2.105 at thee center of the lower end 2.43 to allow the patient to be attached to a portable oxygen system or the like and moved at anytime, and a pair of side, or drainage connection, ports 2.107 on either side of the bottom center port 2.105 at the lower end 2.43 for use in flushing collected drainage from the cavity 233 or the like. Each of the ports 2.101, 2.103, 2.105, 2.107 communicates with the cavity 2.33. For example, the appliance 2.11 is shown in FIG. 33 with a typical hospital room pressurized oxygen line HO connected to one of the side ports 2.101 via a typical a quick-connect connection C. The appliance 2.11 is shown in FIG. 35 with a typical portable oxygen supply line PO connected the bottom center port 2.105 via a typical quick-connect connection C. The appliance 2.11 is shown in FIG. 36 with typical suction drainage lines SL connected to both bottom side ports 2.107 via typical quick-connect connection C.

The appliance 2.11 may include elbow extension members 2.109 for being attached to either side portion 2.101 for oxygen use. Each elbow extension member 2.109 preferably has an 90° end and can be adjusted up or down, etc.

The appliance 2.11 may include an airway mouthpiece 2.111 for being attached to the body 2.25 of the housing member 2.21 in communication with the center port 2.103 to allow cardiopulmonary resuscitation (CPR) if necessary.

The appliance 2.11 may include a valve 2.51 for controlling the passage of air between the airway opening of the body 2.25, the cavity 2.33, and the cavity 2.31 of the stoma tube 2.23. The valve 2.51 preferably includes a rotatable gate 2.53 for regulating the volume of air passing from the cavity 2.33 through the cavity 2.31 into the patient's trachea T. The rotatable gate 2.53 has a cylindrical body portion 2.55 for fitting into and substantially plugging the center port 2.103 of the body 2.25 and the end of the cavity 2.31 at the second end 2.29 of the stoma tube 2.23. A T-shaped aperture 2.57 extends through the body portion 2.55 to allow the passage of air between the cavities 2.31, 2.33 so that rotation of the body portion 2.55 effectively controls the passage of air between the airway opening of the body 2.25, the cavity 2.33, and the cavity 2.31 of the stoma tube 2.23. A handle or tab 2.59 is preferably attached to the body portion 2.55 outside the body 2.25 to allow the patient P to easily rotate the body portion 2.55 and control the passage of air to his/her lungs, etc. The exterior surface of the body portion 2.55 may have a thread like ridge 2.60 for engaging portions of the housing member 2.21 to form a substantially air tight connection therebetween.

The appliance 2.11 may include an elongated airway or trachea tube 2.115 attached to the first end 2.27 of the stoma tube 2.23 for insertion into the patient's trachea T. The trachea tube 2.115 is preferably substantially rigid and stationary, but preferably has a flexible elbow or midportion 2.117 to allow flexible bending thereof, if necessary, to properly insert the trachea tube 2.115 into the patient's trachea T. The length of the trachea tube 2.115 can be adjusted by merely cutting off any excess length thereof. The trachea tube 2.115 may be made separate from the stoma tube 2.23 and merely fixedly secured thereto in any manner now apparent to those skilled in the art. Preferably, however, the trachea tube 2.115 is molded or otherwise constructed as a one-piece, integral unit with the housing member 2.21.

The appliance 2.11 preferably includes an airway access tube 2.119 for being selectively attached to the body 2.25 of the housing member 2.21 in communication with the cavity 2.33 thereof substantially aligned with the cavity 2.31 of the stoma tube 2.23 of the housing member 2.21. More specifically, the distal end of the airway access tube 2.119 can be inserted into the center port 2.103 of the body 2.25 and, if desired, into the cavity 2.29 of the stoma tube 2.23. The airway access tube 2.119 preferably has a flexible elbow 2.121. The airway access tube 2.119 will serve as an oxygen tube. The airway access tube 2.119 may be molded or otherwise constructed from a lightweight pliable plastic or rubber.

The appliance 2.11 preferably includes cap means 2.123 for selectively closing the ports 2.101, 2.105, 2.107, and the airway access tube 2.119. Each cap means 2.123 preferably includes a cap 2.125 sized to tightly fit over and close the open ends of the respective port 2.101, 2.105, 2.107 or airway access tube 2.119, when not in use. Each cap 2.125 is preferably solid plastic and is preferably movably secured to the respective port 2.101, 2.105, 2.107 or airway access tube 2.119 by way of a harness ring 2.127 that can be slid over the respective port 2.101, 2.105, 2.107 or airway access tube 2.119, and a flexible strap 2.129 extending between each cap 2.125 and ring 2.127, so that the cap 2.125 will not be misplaced. Each cap 2.125 may be color coded for safety and simplicity of use, etc.

The appliance 2.11 preferably includes filter means 2.131 for selectively covering the side ports 2.101, 2.107 of the body 2.25 of the housing member 2.21 to filter any air entering therethrough. Each filter means 2.131 preferably includes a filter element 2.133 sized to tightly fit over the open end of a respective port 2.101, 2.107, and to hold a filter media portion 2.135. Each filter element 2.133 preferably has an element face consisting of an open grid for holding a filter media portion 2.135 in place while allowing airflow therethrough. The filter means 2.131 will prevent unfiltered air from entering the stoma S and the patient's lungs.

To use the multi use appliance 2.11, the protective cover 2.13 is attached to the patient's neck N with the aperture 2.15 through the protective cover 2.13 positioned over the mouth of the stoma S. The first end 2.27 of the stoma tube 2.23 can then be inserted into the stoma S until the gasket 2.61 forms a seal between the protective cover 2.13 and the housing member 2.21. To use the appliance 2.11 in a manner which allows the patient P to regulate the flow of air through the appliance 2.11 and into the trachea T, the body portion 2.55 of the rotatable gate 2.53 of the valve 2.51 is merely inserted into the center port 2.103 of the body 2.25 of the housing member 2.21 to thereby allow the patient P to regulate the airflow by merely rotating the tab 2.59. The caps 2.125 can be removed from the side ports 2.101 to allow air to flow in through the side ports 2.101, through the filter means 2.131, and through the aperture 2.57 in the body portion 2.55 of the gate 2.53 of the valve 2.51 and into the stoma tube 2.23. Various oxygen, gas or vacuum lines can be connected to respective ports 2.101, 2.105, 2.107 when desired. To then use the appliance 2.11 for CPR, the valve 2.51 is merely removed and the airway mouthpiece 2.111 inserted into the center port 2.103. To use the appliance 2.11 for emergency airway access and tracheostoma, the trachea tube 2.115 is attached to the stoma tube 2.23 and inserted into the patient's trachea T. The airway access tube 2.119 can be used in combination with the trachea tube 2.115 to serve as an oxygen tube.

Although the present invention has been described and illustrated with respect to preferred embodiments and preferred uses therefor, it is not to be so limited since modifications and changes can be made therein which are within the full intended scope of the invention.

What is claimed is:

1. An appliance for a stoma extending through a patient's neck into the patient's trachea said appliance comprising:
   a) a protective cover for attachment to the patient's neck about the stoma, said protective cover having an aperture therethrough for positioning over the entrance of the stoma when said protective cover is attached to the patient's neck adjacent the stoma;
   b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity; said housing member including a divider wall within said cavity of said body of said housing member for dividing said cavity of said body of said housing member into a discharge chamber for receiving waste through said stoma tube from the patient's trachea and an airway chamber for allowing air to pass from said airway opening of said body of said housing member through said cavities of said body of said housing member and said stoma tube of said housing member and into the patient's trachea; and
   c) a gasket for forming a seal between said protective cover and said housing member.

2. The appliance of claim 1 in which said divider wall extends at least partway into said cavity of said stoma tube.

3. The appliance of claim 1 in which is included a stoma cover pad for covering said stoma.

4. An appliance for a stoma extending through a patient's neck into the patient's trachea; said appliance comprising:
   a) a protective cover for attachment to the patient's neck about the stoma, said protective cover having an aperture therethrough for positioning over the entrance of the stoma when said protective cover is attached to the patient's neck adjacent the stoma;
   b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity; and
   c) a gasket for forming a seal between said protective cover and said housing member;
   d) filter means for filtering air passing through said airway opening of said body of said housing member; said filter means being removable from said body of said housing member; and
   e) an oxygen connection coupled with said filter means for allowing pressurized oxygen from a pressurized oxygen supply means to flow into said cavity of said body of said housing member.

5. The appliance of claim 4 in which said oxygen connection includes a tube extending through said filter means, and a cap for selectively closing said tube.

6. An appliance for a stoma extending through a patient's neck into the patient's trachea; said appliance comprising:
   a) a protective cover for attachment to the patient's neck about the stoma, said protective cover having an aperture therethrough for positioning over the entrance of the stoma when said protective cover is attached to the patient's neck adjacent the stoma;
   b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity;
   c) a gasket for forming a seal between said protective cover and said housing member; and
   d) a valve for controlling the passage of air between said airway opening of said body of said housing member, said cavity of said body of said housing member, and said cavity of said stoma tube of said housing member; said valve including a slidable gate for movement between a fully opened position in which the passage of air through said cavity of said body of said housing member is unimpeded, and a fully closed position in which the passage of air through said cavity in said body of said housing member is blocked.

7. An appliance for a stoma extending through a patient's neck into the patient's trachea; said appliance comprising:
   a) a protective cover for attachment to the patient's neck about the stoma, said protective cover having an aperture therethrough for positioning over the entrance of the stoma when said protective cover is attached to the patient's neck adjacent the stoma;
   b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity;

c) a gasket for forming a seal between said protective cover and said housing member; and d) a valve for controlling the passage of air between said airway opening of said body of said housing member, said cavity of said body of said housing member, and said cavity of said stoma tube of said housing member; said valve including a rotatable gate for regulating the volume of air passing from said cavity of said body of said housing member through said cavity of said stoma tube of said housing member.

8. An appliance for a stoma extending through a patient's neck into the patient's trachea; said appliance comprising:

a) a protective cover for attachment to the patient's neck about the stoma, said protective cover having an aperture therethrough for positioning over the entrance of the stoma when said protective cover is attached to the patient's neck adjacent the stoma;

b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity; said body of said housing member having an upper end and a lower end; said upper end of said body of said housing member having a first side port, a second side port, and a center port; each of first side, said second side and said center ports of said upper end of said body of said housing member communicating with said cavity of said body of said housing member; at least one of said first side, said second side and center port of said upper end of said body of said housing member forming said airway opening; said lower end of said body of said housing member having a first side port, a second side port, and a center port; each of said first side, second side and center ports of said lower end of said body communicating with said cavity of said body of said housing member; and c) a gasket for forming a seal between said protective cover and said housing member.

9. The appliance of claim 8 in which is included cap means for selectively closing said first side and second side ports of said upper end of said body of said housing member and said first side, said second side and said center ports of said lower end of said body of said housing member.

10. The appliance of claim 8 in which is included filter means for selectively covering said first and second side ports of said upper end of said body of said housing member.

11. An appliance for a stoma extending through a patient's neck into the patient's trachea; said appliance comprising:

a) a protective cover for attachment to the patient's neck about the stoma, said protective cover having an aperture therethrough for positioning over the entrance of the stoma when said protective cover is attached to the patient's neck adjacent the stoma;

b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity;

c) a gasket for forming a seal between said protective cover and said housing member; and d) a discharge debris pad for attachment to said protective cover below said aperture therethrough for trapping discharge debris from said stoma.

12. The appliance of claim 4 in which said protective cover includes a loop member for holding said discharge debris pad.

13. An appliance for a stoma extending through a patient's neck into the patient's trachea; said appliance comprising:

a) a protective cover for attachment to the patient's neck about the stoma, said protective cover having an aperture therethrough for positioning over the entrance of the stoma when said protective cover is attached to the patient's neck adjacent the stoma;

b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity;

c) a gasket for forming a seal between said protective cover and said housing member; and d) a stoma cover pad for covering said stoma; said protective cover including an upper loop member and a lower loop member for holding said stoma cover pad over said aperture through said protective cover.

14. An appliance for use by a patient having a stoma extending into the patient's trachea; said appliance comprising:

(a) a stoma tube having a first end for extending into the entrance of the stoma, having a second end located remote from said first end thereof, and having a cavity extending between said first and second ends thereof;

(b) a body attached to said second end of said stoma tube; said body having a body cavity communicating with said tube cavity and having an airway opening communicating with said body cavity; and (c) a divider wall within said body cavity for dividing said body cavity into a discharge chamber for receiving waste through said stoma tube from the patient's trachea and an airway chamber for allowing air to pass through said stoma tube into the patient's trachea.

15. An appliance for use by a patient having a stoma extending into the patient's trachea; said appliance comprising:

(a) a stoma tube having a first end for extending into the entrance of the stoma, having a second end located remote from said first end thereof, and having a cavity extending between said first and second ends thereof;

(b) a body attached to said second end of said stoma tube; said body having a body cavity communicating with said tube cavity and having an airway opening communicating with said body cavity;

(c) first filter means including a filter media portion for covering said airway opening of said body to filter air passing through said airway opening of said body; and (d) second filter means including a filter media portion for covering said airway opening of said body in place of said filter media portion of said first filter means to filter air passing through said airway opening of said body, said second filter means including an oxygen connection tube extending through said filter media portion thereof for allowing pressurized oxygen from a pressurized oxygen supply means to flow into said cavity of said body.

16. An appliance for a stoma extending through a patient's neck into the patient's trachea; said appliance comprising:

a) a protective cover for attachment to the patient's neck about the stoma, said protective cover having an aperture therethrough for positioning over the entrance of the stoma when said protective cover is attached to the patient's neck adjacent the stoma;

b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity; said body of said housing member having an upper end and a lower end; said upper end of said body of said housing member having a first port, a second port, and a third port; each of said first, second and third ports of said upper end of said body of said housing member communicating with said cavity of said body of said housing member; at least one of said first, second and third ports of said upper end of said body of said housing member forming said airway opening; said lower end of said body of said housing member having a first port and a second port; each of said first and second ports of said lower end of said body communicating with said cavity of said body of said housing member; and c) a gasket for forming a seal between said protective cover and said housing member.

17. An appliance for a stoma extending through a patient's neck into the patient's trachea; said appliance comprising:

a) a protective cover for attachment to the patient's neck about the stoma, said protective cover having an aperture therethrough for positioning over the entrance of the stoma when said protective cover is attached to the patient's neck adjacent the stoma;

b) a housing member including a stoma tube for extending through said aperture of said protective cover and into the entrance of the stoma, and a body for positioning externally of the stoma; said stoma tube having a first end for extending into the stoma, a second end located remote from said first end thereof, and a cavity extending between said first and second ends thereof; said body of said housing member being attached to said second end of said stoma tube and having a cavity communicating with said cavity of said stoma tube and having an airway opening communicating with said cavity; said body of said housing member having an upper end and a lower end; said upper end of said body of said housing member having port means for communicating with said cavity of said body of said housing member and for forming said airway opening; said lower end of said body of said housing member having port means for communicating with said cavity of said body of said housing member; and c) a gasket for forming a seal between said protective cover and said housing member.

* * * * *